United States Patent [19]
Atkinson et al.

[11] Patent Number: 5,256,145
[45] Date of Patent: Oct. 26, 1993

[54] DILATATION CATHETER STRAIN RELIEF ASSEMBLY

[75] Inventors: Robert Atkinson, St. Anthony; Richard C. Mattison, Plymouth, both of Minn.

[73] Assignee: SciMed Life Systems, Inc., Maple Grove, Minn.

[21] Appl. No.: 852,548

[22] Filed: Mar. 17, 1992

[51] Int. Cl.⁵ .............................. A61M 29/00
[52] U.S. Cl. ........................ 604/96; 604/103
[58] Field of Search ............ 604/96, 95, 97–103; 606/192–194

[56] References Cited
U.S. PATENT DOCUMENTS
4,715,378 12/1987 Pope, Jr. et al. ............... 604/96 X Primary Examiner—John D. Yasko
Attorney, Agent, or Firm—Nawrocki, Rooney & Silvertson

[57] ABSTRACT

A balloon catheter system having a guiding wire, a balloon, and a spring tip joined to a distal end of the guiding wire. A strain relief member covers a portion of the guiding wire between a distal end of the balloon and a proximal end of the spring tip. The strain relief member is defined by a portion of the balloon. Alternatively, the strain relief member comprises a separate tubular member.

22 Claims, 2 Drawing Sheets

DILATATION CATHETER STRAIN RELIEF ASSEMBLY

BACKGROUND OF THE INVENTION

The present invention relates to balloon dilation catheters. In particular, the invention relates to over-the-wire and non-over-the-wire catheters used for angioplasty.

Angioplasty has gained wide acceptance in recent years as an efficient and effective method for treating certain types of vascular diseases. In particular, angioplasty is widely used for expanding a constricted area or stenoses in coronary arteries. It is also used for treatment of stenoses in other parts of the vascular system.

The most widely used form of angioplasty makes use of a dilatation catheter which has an inflatable balloon at its distal end. Using fluoroscopy, a physician guides the catheter through the vascular system until the balloon is positioned across the stenosis. While the catheter is being steered through the vascular system, the balloon is in a deflated state, wrapped (i.e., folded) tightly about the distal end of the catheter to reduce the profile of the balloon so that it can easily traverse arterial vessels and stenoses having small through openings. When the catheter is positioned with the balloon across the stenosis, the balloon is inflated by supplying fluid under pressure through an inflation lumen to the balloon. Inflation of the balloon causes stretching of the artery and pressing of the lesion into the artery wall to reestablish an acceptable blood flow through the artery.

Over-the-wire catheters and non-over-the-wire catheters are two types of dilatation catheters that are commonly used in angioplasty. One type of over-the-wire catheter has an inflation lumen (defined by an outer tube) in fluid flow communication with a balloon member, and a guide wire lumen (defined by an inner tube) through which a separate flexible guide wire is advanced to establish a path to the stenosis. Once a distal end of the guide wire is across the stenosis, the separate over-the-wire catheter is advanced over the guide wire until the balloon is positioned across the lesion.

Typically, the balloon member of the over-the-wire catheter is bonded to the inner tube that defines the guide wire lumen. This bonded region at the distal end of the over-the-wire catheter is a relatively stiff section of an otherwise flexible catheter. The flexible guide wire usually includes an extremely flexible radiopaque spring tip at its distal end. The extreme flexibility of the spring tip allows the guide wire to be steered into and through tortuous arterial branches. Because the relatively stiff bonded region of the over-the-wire catheter is located proximal to the extremely flexible spring tip, there is a potential stress concentration point on the guide wire between the stiff bonded region and the flexible spring tip. Due to the tortuosity of the vascular system through which the guide wire is steered, the guide wire may develop a kink or may weaken due to fatiguing at this stress concentration point. These occurrences may make the guide wire difficult to steer and may unnecessarily prolong the angioplasty procedure.

One type of non-over-the-wire catheter has its own built in flexible guide wire (often referred to as a core wire), such that the core wire, balloon and inflation lumen comprise a single unit. The single unit construction of the non-over-the-wire catheter requires that the catheter be advanced as one element through a patient's vascular system, so as to position the balloon across the lesion. Typically, in a non-over-the-wire catheter, the balloon member is bonded directly to the core wire or to an inner sleeve that is in turn bonded to the core wire. As in the over-the-wire catheter, this bonded region at the distal end of the non-over-the-wire catheter is relatively stiff. Similar to the guide wire of the over-the-wire catheter, the distal end of the flexible core wire of the non-over-the-wire catheter usually includes an extremely flexible radiopaque spring tip. The extreme flexibility of the spring tip allows the non-over-the-wire catheter to be steered into and through tortuous arterial branches. Because the relatively stiff bonded region of the non-over-the-wire catheter is located proximal to the extremely flexible spring tip (as in the over-the-wire catheter), there is a potential stress concentration point on the core wire between the stiff bonded region and the flexible spring tip. Due to the tortuosity of the vascular system through which the non-over-the-wire catheter is steered, the core wire (like the guide wire of the over-the-wire catheter) may develop a kink or may weaken due to fatiguing at this stress concentration point. These occurrences may make the non-over-the-wire difficult to steer and may unnecessarily prolong the angioplasty procedure. One such non-over-the-wire catheter is described in the European Patent Application Publication Number 0 368 523.

It is desirable in both over-the-wire and non-over-the-wire catheters to substantially eliminate the stress concentration point on the guide wire and core wire, respectively, between the relatively stiff bonded region at the distal end of the catheter and the flexible spring tip. The substantial elimination of this stress concentration point would significantly reduce, if not eliminate, kinking and weakening due to fatiguing of the wires.

SUMMARY OF THE INVENTION

The present invention relates to a catheter assembly for inserting an angioplasty balloon into a patient's vascular system and includes a guiding wire having a flexible, helical coil, spring tip joined to its distal end. A balloon assembly is carried at the distal end of the catheter assembly with the spring tip extending beyond the distal end of the balloon assembly. A strain relief member extends from the distal end of the balloon assembly and partially over the spring tip to surround the section of the guiding wire between the distal end of the catheter and the spring tip.

The strain relief member substantially eliminates the stress at the stress concentration point on the guiding wire between the distal end of the catheter and the flexible spring tip. The substantial elimination of this stress significantly reduces, if not eliminates, kinking and weakening (due to fatiguing) of the guiding wire, and thereby substantially eliminates catheter steering difficulties that may be associated with these occurrences.

DETAILED DESCRIPTION OF THE PREFERRED EMBODIMENTS

Figure 1:
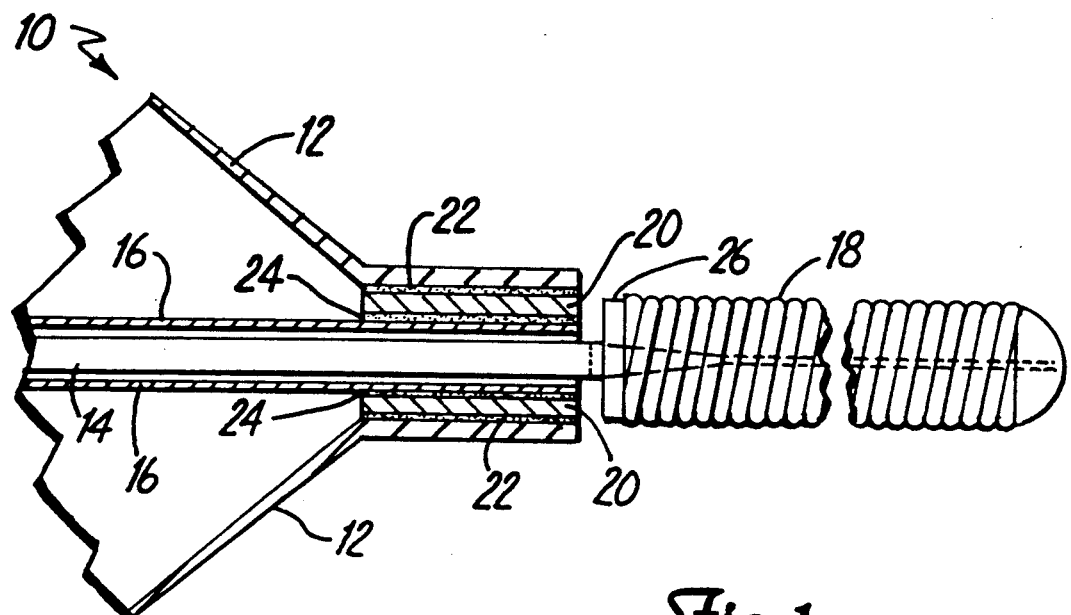
FIG. 1 is a cross-sectional view of a distal end of a prior art balloon catheter.

FIG. 1 is a cross-sectional view of a distal end of a prior art balloon catheter 10. The illustrated portion of the balloon catheter 10 includes a balloon 12 having a distal balloon portion 17, a guiding wire 14 and an inner sleeve 16. The distal balloon portion 17 of the balloon 12 is coupled to the inner sleeve 16 through a collar 20. That is, the collar 20 is bonded to the distal balloon portion 17 with a suitable adhesive and sealing material 22 and to the inner sleeve 16 with a suitable adhesive and sealing material 24. This bonded region 15 at the distal end of the balloon 12 is a relatively stiff section of an otherwise flexible catheter 10.

An extremely flexible spring tip 18 defined by a helical coil 19 is joined to the distal end of the guiding wire 14. A proximal end of the helical coil 19 is joined to a distal end of the guiding wire 14 by a first fused joint 26. A distal end of the helical coil 19 is joined to a shaping ribbon 27 of the guiding wire 14 by a second fused joint 28.

In operation, prior art balloon catheter 10 is inserted into the vascular system of a patient. The extreme flexibility of the spring tip 18 allows the guiding wire 14 and thereby the catheter 10 to be steered into and through tortuous arterial branches. Because the relatively stiff bonded region 15 of the catheter 10 is located proximal to the extremely flexible spring tip 18, there is a stress concentration point 29 (represented by a dotted line in FIG. 1) on the guiding wire 14 between the stiff bonded region 15 and the flexible spring tip 18. Due to the tortuosity of the vascular system through which the catheter 10 is steered, the guiding wire 14 may develop a kink or may weaken due to fatiguing at the stress concentration point 29. These occurrences may make the prior art catheter 10 difficult to steer and may unnecessarily prolong the angioplasty procedure.

Figure 2:
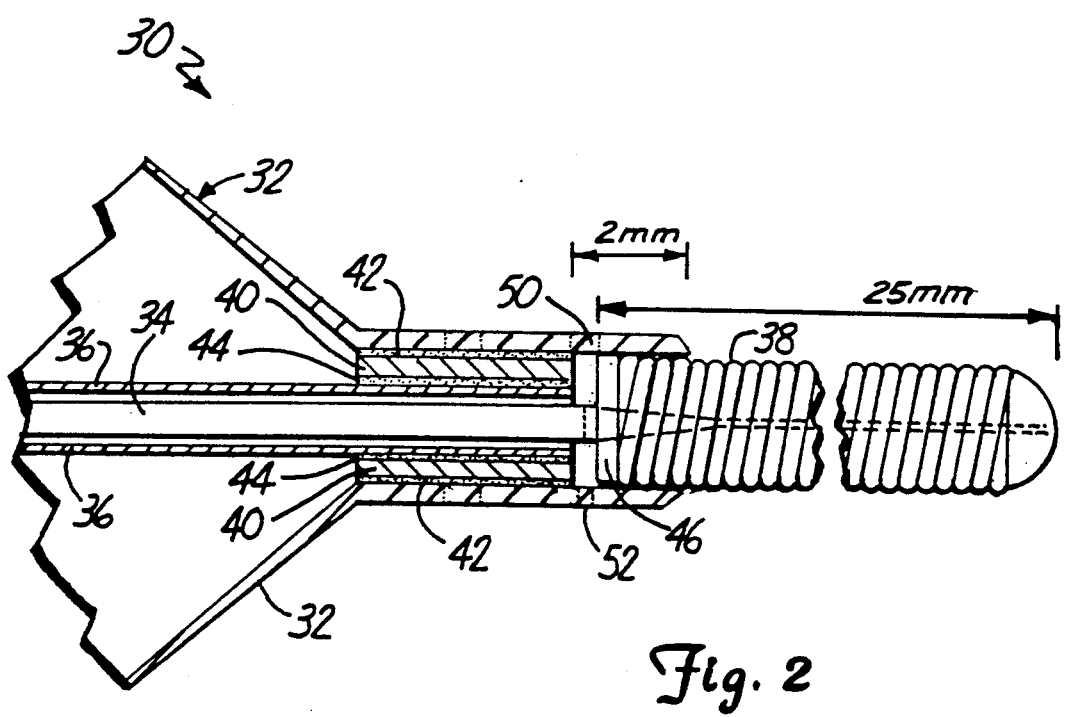
FIG. 2 is a cross-sectional view of the distal end of a balloon catheter in accordance with the present invention.

FIG. 2 shows a cross-sectional view of a distal end of a balloon catheter 30 in accordance with the present invention. Balloon catheter 30 includes an inflatable balloon 32, a flexible guiding wire 34, and an inner sleeve 36. The balloon 32 has a distal balloon segment 37. In one embodiment, the balloon 32 is preferably formed of a polymer material such as polyolefin which has been treated by radiation cross linking. The balloon 32 may also be silicone coated. A suitable polyolefin is available from E.I. DuPont Nemours & Co. (Wilmington, Del.) under the tradename SURYLYN® (8527 POC) Ionomer. The inner sleeve 36 is preferably tubular stock formed from a polyimide, such as is available from HV Technologies, Inc. (Trenton, N.J.). Alternatively, the inner sleeve 36 may be formed from a polyethylene terephthalate (PET).

The flexible guiding wire 34 preferably provides varying flexibility along its length such that its flexibility increases in the distal direction. This may be accomplished by having a guiding wire 34 with one or more ground tapers (not shown). In one embodiment, the guiding wire 34 is preferably formed from Type 304 stainless steel and manufactured by centerless grinding. The guiding wire 34 is preferably stress relieved by exposing the wires before grinding to a temperature in a range of from 500° F. to 800° F. for a time period from about 30 min. to about 6 hours, and preferably at 750° F. for about 5 hours including ramp-up time.

An extremely flexible, radiopaque spring tip 38 defined by a helical coil 39 is joined to the distal end 31 of the guiding wire 34. The helical coil 39 has a proximal end 33 and a distal end 35. The helical coil 39 is preferably formed from radiopaque platinum alloy wire composed of 90% Pt and 10% Ir. A first joint 46 couples the proximal end 33 of the coil 39 to the distal end 31 of the guiding wire 34. The first joint 46 preferably comprises a solder joint consisting of a silver solder material composed of 4% silver and 96% tin. Alternatively, the first joint 46 may comprise a braze joint consisting of a braze material composed of a silver brazing powder with a brazing flux such as (BAg-7-325 mesh) available from Turbo-Braze, Corp. (Union, N.J.). A second joint 47, preferably comprising a weld, connects the distal end 35 of the coil 39 to a shaping ribbon 41 of the guiding wire 34.

A collar 40 provides a spacer between the distal balloon segment 37 and the inner sleeve 36. A suitable adhesive and sealing material 42 bonds an inner surface of the distal balloon segment 37 to an outer surface of the collar 40 while a suitable adhesive and sealing material 44 bonds an inner surface of the collar 40 to an outer surface of the inner sleeve 36. This bonded region 47 at the distal balloon segment 37 (i.e., distal end) of the balloon 12 is a relatively stiff section of an otherwise flexible catheter 30. In one embodiment, the collar 40 is preferably tubular stock formed from a polyimide, such as is available from HV Technologies, Inc. (Trenton, N.J.). Alternatively, the inner sleeve 36 may be formed from a polyethylene terephthalate (PET). The adhesive and sealing materials 42 and 44 are preferably a cyanoacrylate, such as LOCTITE PRISM 405 available from Loctite, Corp. (Newington, Conn.). Alternatively, the adhesive and sealing materials 42 and 44 may be an epoxy, such as TRA-BOND 2135D available from Tra-Con, Inc. (Medford, Mass.).

As seen in FIG. 2, the distal balloon segment 37 of the balloon 32 defines a strain relief portion 48. A through hole 50 extends between an outer surface and an inner surface of the distal balloon segment 37. The through hole 50 is discussed further below. The strain relief portion 48 is that portion of the distal balloon segment 37 of the balloon 32 which extends beyond a distal edge of collar 40 and over a portion of the guiding wire 34 between the proximal end 33 of the spring tip 38 and the distal edge of the collar 40. The portion of the guiding wire 34 between the proximal end 33 of the spring tip 38 and the distal edge of the collar 40 includes stress concentration point 49 (represented by a dotted line in FIG. 2). In addition, the strain relief portion 48 surrounds a proximal portion of spring tip 38.

Strain relief portion 48 provides strain relief to the stress concentration point 49 of the guiding wire 34 distally of the relatively stiff bonded region 47 and proximally to the extremely flexible spring tip 38. More specifically, strain relief portion 48 relieves strain (i.e., stress) applied to stress concentration point 49 of the guiding wire 34 as a result of steering the guiding wire 34 and thereby the catheter 30 through the tortuous vascular system of a patient. Relieving this strain (i.e. stress) substantially reduces, if not eliminates, the stress concentration and thereby kinking and weakening (due to fatiguing) of the guiding wire 34 at the stress concentration point 49.

In a preferred embodiment, the helical coil 39 has varying flexibility and has a length from its proximal end 33 to its distal end 35 of about 25 mm. The strain relief portion 48 has a length of about 2 mm. Alternatively, the helical coil 39 may be 15 mm in length from its proximal end 33 to its distal end 35 with varying flexibility.

The balloon catheter 30 is fabricated using standard procedures except for the use of the through hole 50. During fabrication, the balloon 32 is moved so that through hole 50 in the distal balloon segment 37 is positioned over the collar 40. Adhesive 42 is applied to the region between the distal balloon segment 37 and the collar 40 through the hole 50, as by injection, for example. Additional holes (not shown) may be included in the distal balloon segment 37 to facilitate application of the adhesive 42. After the adhesive 42 is applied through the through hole 50, the hole 50 remains positioned over the collar 40 while the adhesive 42 cures. In this preferred embodiment, the hole 50 is spaced apart from the strain relief portion 48 and the strain relief portion 48 (the extension beyond the collar 40) has a length of about 2 mm.

In a variation of the embodiment shown in FIG. 2, after the adhesive 42 is applied through the through hole 50, the balloon 32 is moved distally so that the through hole 50 is distal to the collar 40. This is accomplished by advancing the balloon 32 over the collar 40 after the adhesive 42 is injected but before the adhesive 42 cures.

Figure 3:
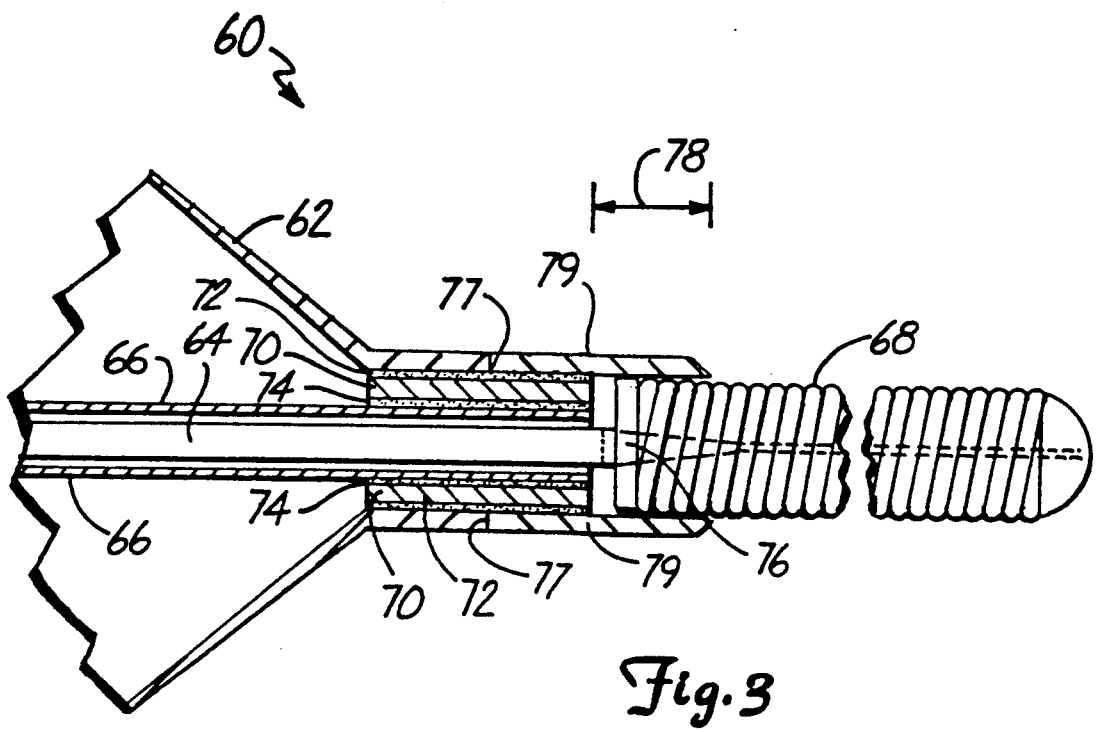
FIG. 3 is a cross-sectional view of the distal end of a balloon catheter made in accordance with another embodiment of the present invention.

FIG. 3 is a cross-sectional view of a distal portion of another balloon catheter embodiment 30A in accordance with the present invention. Balloon catheter 30A includes a balloon 32A, a guiding wire 34A, an inner sleeve 36A, and a spring tip 38A. A collar 40A is connected to the balloon 32A with an adhesive and sealing material 42A and to the inner sleeve 36A with an adhesive and sealing material 44A. The spring tip 38A is coupled to guiding wire 34A at a first joint 46A and to a shaping ribbon 41A of the guiding wire 34A at a second joint 47A.

Balloon catheter 30A shown in FIG. 3 includes a tubular member 79 having a strain relief portion 78 (similar to strain relief portion 48) which covers stress concentration point 49A. Strain relief portion 78 forms a strain relief member as described above in accordance with the present invention. The tubular member 79 is bonded to the balloon 32A by a suitable adhesive and sealing material 77 and to the collar 40A by a suitable adhesive and sealing material 42A. The adhesive and sealing materials 77, 42A and 44A are preferably a cyanoacrylate, such as LOCTITE PRISM 405 available from Loctite, Corp. (Newington, Conn.). Alternatively, the adhesive and sealing materials 77, 42A and 44A may be an epoxy, such as TRA-BOND 2135D available from Tra-Con, Inc. (Medford, Mass.).

In the embodiment shown in FIG. 3, adhesives 77 and 42A are injected before tubular member 79 is connected to balloon 32A. The embodiment of FIG. 3 eliminates the hole 50 required in the embodiment shown in FIG. 2. Typically, the spring tip 38A has a length of about 25 mm (with varying flexibility) and portion 78 (the extension of member 79 beyond collar 40A) has a length of about 2 mm. In a preferred embodiment, tubular member 79 has a length of about 3 mm. Alternatively, the spring tip 38A may be 15 mm in length with varying flexibility.

Figure 4:
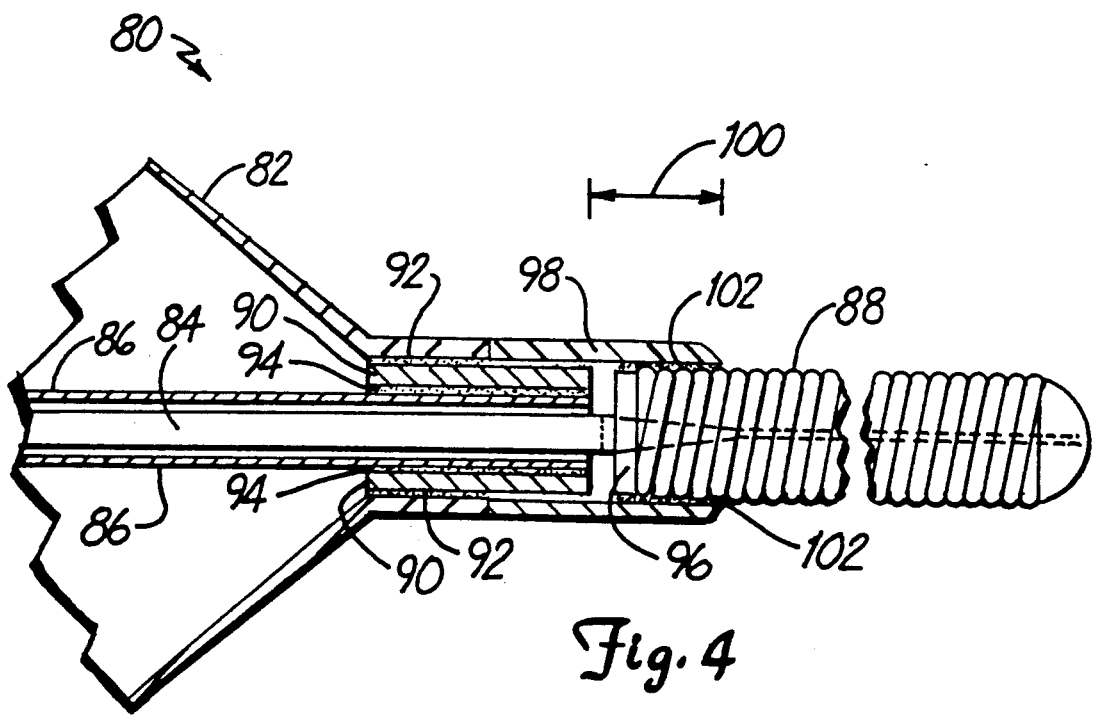
FIG. 4 is a cross-sectional view of the distal end of a balloon catheter made in accordance with still a further embodiment of the present invention.

FIG. 4 shows another balloon catheter embodiment 30B in accordance with the present invention. Balloon catheter 30B of FIG. 4 includes a balloon 32B, a guiding wire 34B, an inner sleeve 36B, and a spring tip 38B. Balloon 32B is coupled to inner sleeve 36B by a collar 40B. The collar 40B is secured to balloon 32B with an adhesive and sealing material 42B and to inner sleeve 36B with an adhesive and sealing material 44B. The spring tip 38B is joined to guiding wire 34B at first and second joints 46B and 47B, respectively.

The balloon catheter 30B shown in FIG. 4 includes a tubular member 98 which extends over the collar 40B. Tubular member 98 includes strain relief portion 100 which extends over a proximal portion of the spring tip 38B and over the stress concentration point 49B of the guiding wire 34B. The strain relief portion 100 of tubular member 98 forms a strain relief member as described above in accordance with the present invention. Tubular member 98 is bonded to a proximal portion of the spring tip 38B with a suitable adhesive and sealing material 102. Tubular member 98 is not bonded to balloon 32B or collar 40B. Adhesive 42B is applied before tubular member 98 is mounted and thereby eliminates the need for an injection through hole 50 as shown in FIG. 2. The adhesive and sealing materials 102, 42B and 44B are preferably a cyanoacrylate, such as LOCTITE PRISM 405 available from Loctite, Corp. (Newington, Conn.). Alternatively, the adhesive and sealing materials 102, 42B and 44B may be an epoxy, such as TRA-BOND 2135D available from Tra-Con, Inc. (Medford, Mass.). In a preferred embodiment, spring tip 38B has a length of about 25 mm (with varying flexibility), strain relief portion 100 has a length of about 2 mm and tubular member 98 has a length of about 3 mm. Alternatively, the spring tip 38B may be 15 mm in length with varying flexibility.

The above described strain relief members substantially eliminate the stress at the stress concentration point on the guiding wire between the distal end (i.e., the relatively stiff bonded region) of the catheter and the flexible spring tip. The substantial elimination of this stress significantly reduces, if not eliminates, kinking and weakening (due to fatiguing) of the guiding wire, and thereby substantially eliminates catheter steering difficulties that may be associated with these occurrences.

Although the present invention has been described with reference to preferred embodiments, workers skilled in the art will recognize that changes may be made in form and detail without departing from the spirit and scope of the invention. For example, in considering a preferred commercial embodiment of the catheter of the present invention, it is contemplated that the strain relief assembly would be included on catheters as disclosed in the commonly assigned applications entitled (1) Balloon Dilatation Catheter Having A Free Core Wire (Ser. No. 07/852,545); (2) Balloon Dilatation Catheter, Having A Torsionally Soft Component (Ser. No. 07/852,547); and (3) Balloon Dilatation Catheter Having Dual Sealing Plugs (Ser. No. 07/852,546), which have been filed on even date with this application and which are hereby incorporated herein in their entirety by reference thereto.

What is claimed is:

1. In a catheter system having an inflatable balloon with a distal end, a guiding member and a spring tip having a proximal end, the spring tip being joined to the guiding member distally of the distal end of the balloon, the improvement comprising:

a strain relief member extending between the balloon and the spring tip and surrounding at least a portion of the guiding member between the distal end of the balloon and the proximal end of the spring tip, such that strain at the portion of the guiding member distally of the distal end of the balloon and proximally of the proximal end of the spring tip is reduced.

2. An angioplasty balloon catheter system, comprising:

an inflatable balloon having a distal end, the balloon being coupled to a distal end of the catheter system;

an inner sleeve extending through at least a portion of the balloon and having a distal end;

a guiding wire extending through the inner sleeve and the distal end of the inner sleeve;

guide means coupled to a distal end of the guiding wire; and a strain relief member adjacent the guide means and free from any fixed connection between the balloon and the guiding wire, the strain relief member surrounding at least a portion of the guiding wire for relieving strain from the guiding wire in a region between the distal end of the balloon and the guide means.

3. The angioplasty balloon catheter system of claim 2 including a collar arranged about distal end of the inner sleeve.

4. The angioplasty balloon catheter system of claim 3 wherein the balloon includes at least one hole through which an adhesive is injected between the balloon and the collar.

5. The angioplasty balloon catheter system of claim 2 wherein the strain relief member comprises a strain relief portion of the balloon.

6. The angioplasty balloon catheter system of claim 2 wherein the strain relief member comprises a separate tube.

7. The angioplasty balloon catheter system of claim 6 wherein the separate tube is bonded to a collar arranged about the distal end of the inner sleeve.

8. The angioplasty balloon catheter system of claim 6 wherein the separate tube is bonded to the spring tip.

9. The angioplasty balloon catheter system of claim 2 wherein the strain relief member has a longitudinal length of about 2 mm.

10. An angioplasty balloon catheter system, comprising:

a guiding wire having a distal end;

a helical coil, spring tip coupled to the distal end of the guiding wire, the spring tip having a proximal end;

an inner sleeve extending coaxially and aligned with the guiding wire, the inner sleeve having a distal end;

a collar arranged about the distal end of the inner sleeve;

a balloon having a distal end coupled to the collar; and a strain relief member arranged about the guiding wire along a portion of the guiding wire between the distal end of the inner sleeve and the proximal end of the spring tip for absorbing guiding wire strain proximally of the proximal end of the spring tip.

11. The angioplasty balloon catheter system of claim 10 wherein the strain relief member comprises a strain relief portion of the balloon.

12. The angioplasty balloon catheter system of claim 10 wherein the balloon includes at least one hole through which an adhesive is injected between the balloon and the collar.

13. The angioplasty balloon catheter system of claim 10 wherein the strain relief member comprises a separate tube.

14. The angioplasty balloon catheter system of claim 13 wherein the separate tube is bonded to the collar.

15. The angioplasty balloon catheter system of claim 13 wherein the separate tube is bonded to the helical coil spring tip.

16. The angioplasty balloon catheter system of claim 10 wherein the strain relief member has a longitudinal length of about 2 mm.

17. An angioplasty balloon catheter, comprising:

an elongated guiding wire having a distal end;

guide means coupled to the distal end of the guiding wire for guiding the elongated guiding wire through a vascular system of a patient, the guide means having a proximal end;

an elongated inner sleeve extending coaxially with the guiding wire and having a distal end adjacent the distal end of the guiding wire;

a collar arranged about the distal end of the inner sleeve and bonded to the inner sleeve;

a balloon arranged about the inner sleeve and bonded to the collar; and a strain relief member free from any fixed connection with at least one of the balloon and the guide means and extending from the collar over the guide means and covering the guide means, the strain relief member receiving force applied to the guiding wire between the proximal end of the guide means and the balloon.

18. The angioplasty balloon catheter of claim 17 wherein the strain relief member is formed from a portion of the balloon.

19. The angioplasty balloon catheter of claim 17 wherein the strain relief member includes at least one hole through which an adhesive is injected onto an outer surface of the collar.

20. The angioplasty balloon catheter of claim 17 wherein the strain relief member comprises a separate tubular member.

21. The angioplasty balloon catheter of claim 20 wherein the separate tubular member is bonded to the collar.

22. The angioplasty balloon catheter of claim 20 wherein the separate tubular member is bonded to the guide means.

* * * * *